United States Patent
Steigmiller et al.

(10) Patent No.: US 8,431,089 B2
(45) Date of Patent: Apr. 30, 2013

(54) PROCESS ANALYSIS SYSTEM WITH STERILE SAMPLING OF MECHANICALLY-SENSITIVE MATERIAL FROM A BIOREACTOR

(75) Inventors: Stefan Steigmiller, Bergisch Gladbach (DE); Hans Tups, Bergisch Gladbach (DE); Karsten Sommer, Krefeld (DE); Sonja Danstedt, Neuss (DE); Martin Schiffhauer, Erkrath (DE); Sebastian Schmidt, Haan (DE); Jörg Kauling, Köln (DE); Arndt Braun, Remscheid (DE)

(73) Assignee: Bayer Technology Services GmbH, Leverkusen (DE)

( * ) Notice: Subject to any disclaimer, the term of this patent is extended or adjusted under 35 U.S.C. 154(b) by 36 days.

(21) Appl. No.: 12/297,831

(22) PCT Filed: Apr. 17, 2007

(86) PCT No.: PCT/EP2007/003341
§ 371 (c)(1),
(2), (4) Date: Dec. 10, 2008

(87) PCT Pub. No.: WO2007/121887
PCT Pub. Date: Nov. 1, 2007

(65) Prior Publication Data
US 2009/0178495 A1    Jul. 16, 2009

(30) Foreign Application Priority Data
Apr. 21, 2006 (DE) .......................... 10 2006 019 242

(51) Int. Cl.
*B01L 3/00* (2006.01)

(52) U.S. Cl.
USPC ............. 422/502; 422/50; 422/504; 422/505; 436/180

(58) Field of Classification Search ............ 422/99–100, 422/63, 50, 502, 504–505; 436/180
See application file for complete search history.

(56) References Cited

U.S. PATENT DOCUMENTS

| 5,630,935 | A  | * | 5/1997 | Treu ............................ 210/130 |
| 6,814,102 | B2 | * | 11/2004 | Hess et al. .................. 137/625.5 |
| 6,871,669 | B2 | * | 3/2005 | Meyer et al. .................. 137/862 |
| 2002/0132355 | A1 | | 9/2002 | Schembri |
| 2004/0259241 | A1 | | 12/2004 | Barringer |

FOREIGN PATENT DOCUMENTS

| DE | 20 316 936 | 3/2004 |
| DE | 203 16 936 | 3/2004 |
| EP | 1 439 472 | 7/2004 |

(Continued)

OTHER PUBLICATIONS

"Process Analytical Liquid Chromatography"; DX-800 Process Analyzer; Reagent-Free IC—Dionex Process Analytical.

*Primary Examiner* — Jyoti Nagpaul
(74) *Attorney, Agent, or Firm* — Norris McLaughlin & Marcus PA

(57) ABSTRACT

Sampling valve with which samples containing mechanically sensitive material are removed in a sterile manner from a bioreactor, and process analysis system with analysis stations, in particular chromatography systems, biosensors and cell determination devices, permitting automated, sterile removal of a sample from a bioreactor and gentle transport of the sample, containing mechanically sensitive material, in particular cells, to the analysis station.

15 Claims, 7 Drawing Sheets

FOREIGN PATENT DOCUMENTS

| | | |
|---|---|---|
| FR | 2 617 286 | 12/1988 |
| JP | 56-161493 | 10/1981 |
| JP | 03-110435 | 12/1991 |
| WO | 90 12972 | 11/1990 |
| WO | 2004044119 | 3/2004 |

\* cited by examiner

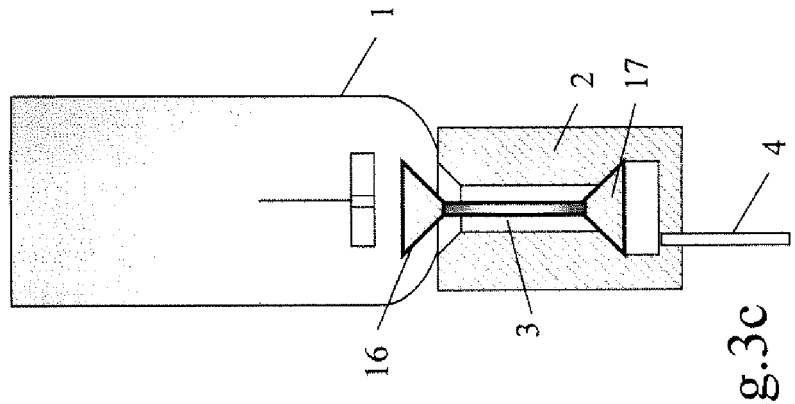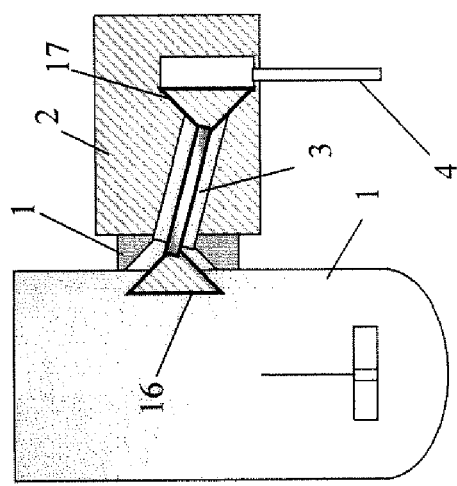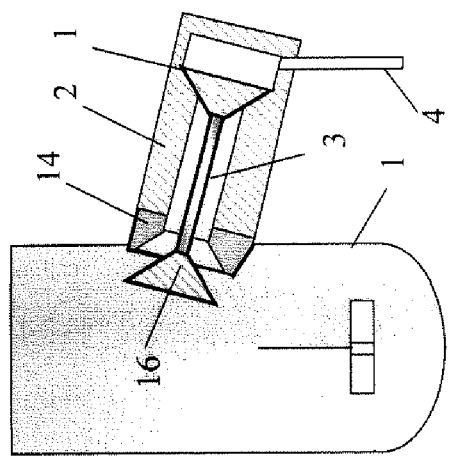

PROCESS ANALYSIS SYSTEM WITH STERILE SAMPLING OF MECHANICALLY-SENSITIVE MATERIAL FROM A BIOREACTOR

This is a 371 of PCT/EP2007/003341 filed 17 Apr. 2007 (international filing date), which claims foreign priority benefit under 35 U.S.C. §119 of German Patent Application No. 10 2006 0019 242.7 filed Apr. 21, 2006

The invention relates to a sampling valve with which samples containing mechanically sensitive material are removed from a reactor, and to a process analysis system with analysis stations, in particular chromatography systems, biosensors and cell determination devices, permitting automated, sterile removal of a sample from a bioreactor and gentle transport of the sample, containing mechanically sensitive material, in particular cells, to the analysis station.

BACKGROUND OF THE INVENTION

Sterile sampling is a standard procedure in fermentation processes. It is the first operating step on the path to sample analysis for determining or detecting the state and quality of a bioprocess and, in particular, of the products arising from the latter. In this connection, it has hitherto been necessary, in many cases, for a laboratory technician to remove a sample manually. Delivery of the sample to a central analysis station is followed by sample preparation, i.e. biomass separation and aliquoting, and, finally, by the analysis on several different analysis devices. The analysis results are printed out for documentation of product quality and are input manually into databases and stored. Moreover, suitably identified reserve specimens are stored at low temperatures for subsequent detection methods. The analysis results are checked in the quality assurance system in order to release the product obtained in a bioprocess or to discard it because of quality defects. All of these steps are very labor-intensive and accordingly result in high costs. The process in the reactor is usually controlled and regulated after manual input of the analysis results obtained. Complete automation of process control and regulation is therefore not possible.

To reduce the number of staff needed, numerous automated individual components are now available on the market, e.g. sterile sampling devices, pipetting systems and automatic analyzers. However, complete automation of sampling and analysis is impossible because of the fact that samples have hitherto been transported exclusively by personnel from the production site to a separate laboratory for quality control, and because of the resulting break in the chain of automation. Moreover, laboratory analysis does not provide real-time information that would permit control of the process.

EP 1439472 A1 describes automatic process analysis, control and regulation, in particular by process chromatography, in chemistry and polymer science, where no particular demands are placed on sterility. The solution described does not satisfy the requirements of treating mechanically sensitive material, in particular biological material, and in particular living cells. The described process analysis system is unsuitable for most bioapplications.

Process chromatography for bioapplications is described in US 2004259241 A1 (Groton Biosystems). The described sampling device is limited to laboratory-scale bioreactors, since it is not sterilizable by steam, which is the usual sterilization method used in production. Moreover, Dionex Corporation offers the DX-800 process chromatograph (product brochure "DX-800 Process Analyser, Process Analytical Liquid Chromatography") which can be operated for process control of bioapplications. This system offers automated chromatography, but no sampling that corresponds to the strict demands of sterilization technology on bioreactors. This system is additionally limited to the analysis of cell-free media. Both systems are designed for determination of several parameters. However, they do not provide an integrated solution for sampling, in particular of shear-sensitive material, e.g. cells, and no control and regulation of a bioprocess via the obtained data, since important automation units for connection to a process control system are lacking.

A further common disadvantage of the two systems described above for biotechnology applications is, in addition to there being no possibility of sterilization by steam, the fact that they are suitable only for sample preparation for a specific biochromatography process. Such systems cannot be used flexibly for other analysis methods, and instead are used exclusively for the particular biochromatography process described.

Sampling devices, and in particular sampling valves, for bioprocesses for removal of biological material and in particular cells are known as prior art, and some are even available commercially. For example, WO 1990012972 A1, from the company Keofitt a/s, describes a sampling valve composed of two parts, namely a valve body and a valve head. Inside the valve body, two connectors are connected via an annular channel about a rubber membrane. This structure allows the valve to be sterilized before and after use. WO 2004044119 A1 from Sartorius BBI Systems GmbH describes a coolable sampling valve with a cylindrical flow channel and a ram for blocking the flow channel, the walls of the sampling valve being made of a material of low thickness, usually of metal, in particular stainless steel, in order to permit rapid cooling of the valve, e.g. after steam sterilization. WO 1990012972 A1 and WO 2004044119 A1 do not describe the transport of the removed sample. A disadvantage of the two abovementioned sampling valves from WO 1990012972 A1 and WO 2004044119 A1 is that both have a metal-metal contact interface between the head of the sampling valve and the bioreactor, and, in the case of steam sterilization of the sampling valve, this causes local heating of the medium in the bioreactor, such that more cell aggregates may occur at the sampling site (so-called biofouling). When the described sampling valves are opened, such aggregates, which occur also during normal operation of a bioreactor, may swirl up and pass into the valve. To avoid clogging, transport conduits with relatively large diameters are therefore needed for transporting the removed cell suspension. In addition, the volume of the sample is determined exclusively by adjusting the opening time of the sampling valve. The solution does not permit precise removal of a predefined volume and in particular of a small volume. Moreover, no sample transport of a small cell-containing volume over a long distance is hitherto known without this sample, during transport, being adulterated, e.g. by sedimentation during transport or by destruction of cells by shearing.

There was therefore a need to make available an automatic and flexible process analysis system for control and regulation of bioprocesses with integrated connection to automation systems, which process analysis system permits sampling, gentle transport and preparation of small sample volumes containing mechanically sensitive material such as biological material, in particular living cells, and into which process analysis system a classical biochromatography system and/or further analyzers can be integrated. The process analysis system should be able to be operated under sterile conditions, and valves and transport conduits should be able to be sterilized as far as possible with steam, without causing heating of the reactor medium.

SUMMARY OF THE INVENTION

A first subject matter of the present invention is a sampling valve for removing a sample of defined volume, in particular of biological material, and in particular of living cell material, with reduced mechanical loading, in particular as a result of shearing forces.

DETAILED DESCRIPTION

A particular embodiment of the sampling valve comprises a preferably cylindrical sample chamber of defined volume, delimited by a front sealing element and a rear sealing element. The front sealing element is normally actuated by a connection shaft. The front sealing element is opened in the direction of the interior of the bioreactor, and, preferably at the same time, the rear sealing element is closed relative to the sample chamber. In this opened state of the valve, the air bubble enclosed in the sample chamber escapes into the reactor, and a sample of defined volume flows from the bioreactor into the sample chamber. The rear sealing element limits the sampling volume and permits removal of a defined volume. The closure force can be transmitted by pretensioning of a spring, preferably a spiral spring, from a pressure plate to the rear sealing element via a connection rod, said rear sealing element providing sealing by being pressed against a valve stem by means of a sealing device, preferably an O-ring. The pretensioning is usually set to a differential pressure between sample chamber and reactor of at least +1.5 bar. Therefore, at said pretensioning of the spring, an underpressure or vacuum in the bioreactor does not lead to unintentional opening of the valve, nor does it increase the internal pressure in the reactor relative to the external pressure (e.g. during autoclaving), which may additionally intensify the closure force. The sampling valve is preferably opened by actuation of a lifting cylinder. After release of the lifting cylinder via a control, which can take place pneumatically (control by compressed air) or electrically (by an impulse), preferably pneumatically, the valve closes in fractions of a second after the closure command has been issued, this short delay ensuring the precise volume of the sample. A guide rod mounted on the connection shaft can serve for secure positioning of the sealing surfaces. When the sampling valve is opened, a pressure force directed counter to the restoring force of the spring can be transmitted to the guide rod. A membrane is usually fitted on this guide rod and can be kept squeezed between two retainer plates. The pressure force on the guide rod leads to deflection of the membrane, which hermetically seals off the sample chamber and a rear valve interior from the environment. To reduce the loading of the membrane, the rear valve interior preferably has a greater diameter than the sample chamber.

In a particular embodiment of the invention, the sampling valve on the probe head (the opening to the reactor) is protected by a self-cleaning filter, such that no large aggregates can enter the sample chamber and the transport conduit. The width of the pores of this filter is usually 0.02 µm to 2 mm, but preferably 0.45 µm to 1 mm. In a particular embodiment of the sampling valve, the filter has a hollow chamber which, in the closed state, is filled from the inside by a cap around the front sealing element, i.e. the pores are closed off from the inside by the cap. In the opened state, the cap is moved out in the direction of the reactor, resulting in the formation of an opened area.

The membrane is preferably made of a material resistant to water vapor, preferably EPDM, silicone, HNBR or PFR plastics. The probe head is preferably made of a plastic approved for pharmaceutical applications, preferably PVDF, PEEK or POM, which has a lower heat conductivity than stainless steel and on which cells adhere particularly poorly. Thus, there is no metal-metal contact interface to the attached reactor, such that it is possible to avoid local heating of the bioreactor and fouling layers on the sealing device, which is preferably an O-ring, during the cleaning process, e.g. by steam sterilization.

A small sampling volume is imperative for frequent sampling. With the aid of the sampling valve according to the invention, it is possible to remove exactly defined volumes of 2 ml to 200 ml, preferably of between 5 ml and 20 ml.

The sampling valve according to the invention, analogously to standard probes, is usually fitted with the aid of a screw connection into standardized fermenter nozzles, preferably with the diameter of DN25, usually with the aid of a sealing device, preferably with what is called an O-ring. To improve the run-off behavior of the sample and of the cleaning liquids to be used at a later stage, a downwardly inclined installation of the sampling valve on the bioreactor wall is advantageous. Favorable installation angles are between 0° and 90° to the horizontal, preferably between 1° and 15°.

In another preferred embodiment of the valve, the cylindrical sample chamber can itself be inclined relative to the nozzle axis, preferably between 1° and 15° to the horizontal.

If necessary, the sampling valve according to the invention can be temperature-controlled, for which purpose the sampling valve is preferably encased and temperature-controlled by a Peltier element.

After closure of the valve, the path to an attached transport conduit is freed. The sample is then transported as a substantially continuous plug to the target location, e.g. a sample preparation and/or analysis station. For transporting the sample, gas and liquid are usually introduced through an admission opening and a channel and slowly move the sample from the sample chamber into a rear valve interior and to a discharge nozzle. The admission opening can be protected by a valve, preferably a check valve.

The sampling valve is usually coupled to transport and supply conduits, in particular cleaning conduits. The coupling is preferably effected using autoclavable and steam-sterilizable quick-closure couplings which, in the disengaged state, have a closure mechanism that protects the sterile inner surfaces of the two coupling pieces against contamination.

According to a particular embodiment of the invention, a cock, preferably a three-way cock, is integrated between the sampling valve and the transport conduit, allows a sample to be removed manually, preferably has a control unit and can be operated decentrally.

A further subject matter of the present invention is a process analysis system which comprises at least one device for removal of a sample from a reactor, a sample-transporting device and at least one sample analysis station, allowing a volume of sample material to be removed from the reactor and transported to the analysis station, said sample material being a suspension of mechanically sensitive material, in particular shear-sensitive material, which is exposed to reduced mechanical loading, in particular reduced shearing forces. Preferably, the volume is precisely defined and/or aggregate-free.

Mechanically sensitive material, in particular shear-sensitive material, within the meaning of the present invention is in particular biological material, e.g. cells, bacteria, single-cell fungi such as yeasts, viruses, agglomerates of protein precipitates, protein crystals, native proteins, antibodies, liposomes and, in particular, living animal and/or plant cells.

The process analysis system usually comprises at least one sampling and sample-transporting device connected to at least one sample preparation and/or sample analysis station.

In a particular embodiment of the process analysis system, the device for automatic sampling is a sampling valve according to the invention.

The process analysis system according to the invention usually controls at least one sample analysis station and has a link to an automation system, preferably to a process control system or programmable controllers for guiding, controlling and/or regulating the process in a reactor, in particular in a bioreactor.

The sampling and sample-transporting devices, the sample preparation station and the process analysis station are preferably of modular design.

The sample preparation stations usually comprise sampling valves, reservoirs, burets, valves, valve islands, dosing valves and the like, which are interconnected by transport conduits and allow the sample to be treated in one or more steps. By suitable operation of the individual modules by a control unit, automatic sample preparation is carried out and controlled. The process analysis system preferably comprises at least one sample preparation station. There, the steps necessary for using the sample for analysis are carried out, e.g. dilution, addition of internal standard, addition of stabilizers (e.g. glycerol), markers or detergent, temperature control, preferably cooling to 4 to 37° C., pH adjustment, stripping, rebuffering, filtration or derivatization. These steps are performed in a fully automated manner and are monitored/controlled by several sensors. Suitable sensors that may be mentioned are, for example, pH electrode, conductivity probe, sensors for measuring optical density, opacity, pressure, temperature, flow.

According to a preferred embodiment of the invention, the process analysis system, and in particular the sample preparation station, includes a sensor-controlled test of the sample to investigate whether the properties of the sample (e.g. cell density) are compatible with the defined operating cycle and in particular with the directions for use of a required analyzer. If the cell density is too high, for example, an analyzer may become blocked. In addition, the cell density may lie outside the measurement range of the analyzer. In this case, the sample is diluted, under sensor control, until reliable quantification of the sample is possible. If, by contrast, the cell density is too low for quantification, a program for increasing the concentration of the sample under sensor control is started.

The sample preparation station preferably has a central collecting vessel in which a sensor for monitoring the sample is integrated, in order to regulate and/or control the treatment of the sample in the sample preparation station. If the sample is highly diluted, a program for increasing the concentration is started, and, if the concentration is too high, a dilution step is initiated. This ensures that measurements of samples or aliquots are not carried out that lie outside the measurement range, the specifications and/or the validated area of the analysis station.

This type of sample preparation can preferably be used to prepare the sample in such a way that an exact analysis can be carried out in an analyzer within the most sensitive measurement range. This permits a more sensitive determination of parameters over a greater concentration range of the sample and, consequently, an improved control of bioprocesses.

The sampling device and the sample analysis station are preferably connected to the sample preparation stations via transport conduits. This creates a modular and integrated system for removal of the samples, transport of the samples, sample preparation and sample analysis. This modular configuration has in particular the advantage that the automatic sample preparation can be configured for different analyzers without great expenditure.

In a particular embodiment of the process analysis system, the sample is divided up into several aliquots in an aliquoting station. These aliquots either pass in succession through one sample preparation station or are transported in parallel into several sample preparation stations where they are treated in different ways. In a further embodiment of the process analysis system, the aliquoting is carried out after the sample preparation, e.g. filtration, decanting, concentration or dilution.

The process analysis system preferably has a central sample preparation station through which the aliquots pass in succession.

After sample preparation, the sample or aliquot is transported into the different sample analysis stations via the transport conduits.

The process analysis system preferably has a self-monitoring facility, which detects and monitors the properties of the sample, preferably temperature, pressure, pH, flow, optical density, conductivity, opacity, in at least one of the different modules.

In a particular embodiment of the process analysis system, the transport of the sample, in particular the flow, optical density or opacity, is monitored and controlled in the transport conduits in order to avoid blockage of the conduits.

The process analysis system is preferably constructed such that, in the event of a power outage or a breakdown, it runs in a secure state that prevents contamination of the content of the connected bioreactors.

The sample analysis station can comprise various sample analyzers, e.g. cell counters, biosensors, spectroscopy systems, chromatography systems, such as HPLC, ion, affinity and/or gel permeation chromatography systems, which are used to examine the sample or aliquot. The analysis results are transferred via a programmable controller and, for example, transmitted via a field bus to an automation unit (e.g. a process control system). The latter can then control and/or regulate the process accordingly. The documentation is managed in accordance with quality assurance requirements.

In a particular embodiment, the sample analyzer carries out biochemical analysis of reaction products or secondary components. Reaction products are generally the proteins that are to be produced, while examples of secondary components are cell state parameters such as vimentin, lactate dehydrogenase or DNA.

In a particular embodiment of the process analysis system, biosensors are incorporated for control of nutrients and metabolism products such as glucose and lactate.

For the biochemical analysis, it is preferable for biological, chemical or biochemical recognition elements, e.g. DNA, RNA, aptamers, receptors, to be bound to biofunctional surfaces, e.g. to the surfaces of microtiter plates, glass surfaces, biosensor surfaces, bead or magnetic bead surfaces, to which elements an analyte specifically binds upon detection by means of a recognition reaction. A widely used method here is the ELISA method. However, biochemical analysis by means of biochemical recognition elements can also take place in homogenous formats in solution, e.g. in the context of homogeneous time-resolved fluorescence (HTRF). Here, the biochemical recognition elements are coupled with signal-generating molecules, e.g. fluorescence dyes or nanoparticles.

Examples of recognition reactions are the binding of ligands to complexes, the complexing of ions, the binding of ligands to (biological) receptors, membrane receptors or ion channels, of antigens or haptens to antibodies (immunoassays), of substrates to enzymes, of DNA or RNA to specific proteins, of aptamers or spiegelmers to their targets, the hybridization of DNA/RNA/PNA or other nucleic acid analogs (DNA assays), or the processing of substrates by enzymes. In the context of DNA assays, the polymerase chain reaction (PCR) method can advantageously be used, particularly preferably the method of kinetic PCR. As signal amplification for immunoassays, the immuno-PCR method can advantageously be used.

Examples of analytes to be detected are DNA, RNA, PNA, nucleic acid analogs, enzyme substrates, peptides, proteins, potential active substances, medicaments, cells, viruses.

Examples of recognition elements, to which the analytes to be detected bind, are DNA, RNA, PNA, nucleic acid analogs, aptamers, spiegelmers, peptides, proteins, complexing agents for metals/metal ions, cyclodextrins, crown ethers, antibodies or their fragments, anticalcins, enzymes, receptors, membrane receptors, ion channels, cell adhesion proteins, gangliosides, monosaccharides or oligosaccharides.

If various recognition elements are bound in a spatially separate manner to the biofunctional surface of the biochemical detection system, a large number of recognition reactions can be carried out simultaneously using one sample. These so-called array technologies are known both for nucleic acid characterization and also for determination of proteins with antibody arrays and can be used to achieve the object according to the invention.

The recognition reaction of the biochemical detection system can be detected by using optical, electrical, mechanical or magnetic signal-transforming methods. Optical methods are particularly preferred, such as chemoluminescence, electrochemoluminescence, absorption detection of an enzymatically induced color change, fluorescence detection of an enzymatically induced conversion of a fluorogenic substrate, Alpha Screen or homogeneous time-resolved fluorescence. Alpha Screen is a homogeneous detection method in which light-induced singlet oxygen is produced on a first bead and, after diffusion to a second bead coupled to the first bead via a biochemical binding reaction, excites it to chemoluminescence.

In another particular embodiment, an autosampler is integrated that collects and cools samples.

According to a preferred embodiment of the invention, this modular structure is also reflected in the control program of the process analysis system. Driver software, preferably for each module, is stored in the control unit of the system, with in-situ operation in a decentralized control and supply unit. The control program of the automation unit accesses this driver software in order to carry out the steps of sterile sampling, automatic sample preparation, analysis and cleaning according to a working procedure predetermined by the user. The delivery of compressed air, steam, cleaning fluids and transport fluids to the sampling valve through the supply and transport conduits is guaranteed and regulated by the control and supply unit.

In a particular embodiment of the process analysis system, several reactors, in particular bioreactors, are operated independently of one another. Each sampling device can be operated in a decentralized manner, via its own control unit, and therefore independently. Furthermore, it is possible for several reactors which work with different cell lines and produce different products to be operated using a single process analysis system and thus particularly inexpensively, since an ingenious cleaning management system prevents mutual contamination of the individual reactors. The process analysis system has a decentralized automation unit with in-situ operation on each sampling device, which are coupled via all standard bus systems to the central programmable controller. In this way, individual units can be switched on and off without any problem.

According to another preferred embodiment of the invention, the procedure of the control program is established by parameters that can be defined by the user. For example, the user can select available modules, and actions to be carried out by them, via a graphical user interface of a conventional personal computer. In this way, procedure sequences for sampling, sample preparation and sample analysis can be defined with the aid of the modules in a tabular form.

The parameters describing this procedure are then exported by a PC and transmitted to the control unit of the regulating system. There, these parameters establish the program procedure of the control program. The parameters thus determine the order in which the control program calls up individual driver programs, and also the control parameters that the control program gives to the driver software in order to make a particular module perform a particular action.

A particular advantage in this case is that a computer expert is not needed for establishing a program procedure of the control program, since the program procedure can take place intuitively via the graphical user interface by selecting modules and the actions to be carried out. In particular, a laboratory assistant or technician can thus use the graphical user interface to describe and trace the steps previously carried out manually by him or her. This description is then used as the parameterization for the control program, such that the latter addresses the respectively required driver software in the necessary order.

According to a preferred embodiment of the invention, an automation component is used as the control unit, for example a Simatic S7 from the company Siemens AG. Such an automation component is designed for problem-free continuous use in an industrial environment and will therefore not "crash" like a conventional PC. A particular advantage in this case is that the PC, with the aid of which the user inputs the procedure, and the control unit can be disconnected from each other during operation of the system. That is to say, the PC can be disconnected from the control unit after the parameters that establish the program procedure have been transmitted from the PC to the control unit. Operation of the control unit independently of the PC is therefore possible.

A further element of the process analysis system according to the invention is the transport device, the purpose of which is to ensure that the sensitive sample of defined volume is conveyed from the sampling device to the preparation or analysis station gently, without becoming blocked, and without loss.

The transport device usually comprises transport conduits and at least one system for gently accelerating the sample or aliquot through the transport conduits.

Consequently, a further subject matter of the present invention is a transport device for transport of suspensions containing mechanically sensitive material and in particular of living cells, comprising transport conduits and at least one system for accelerating the sample or aliquot through the transport conduit from at least two burets, the burets being operated with the following steps:

a) a first buret is filled,
b) shortly before the first buret has reached the limit, a second buret is filled and takes over the transport, the sample experiencing no additional acceleration nor a brief intermediate stop,
c) the first buret is uncoupled from the transport conduits and emptied, such that it is once again available,
d) steps a) to c) are repeated.

The burets are preferably connected with at least one valve island to the transport conduits, the burets and valve island being controlled by the automation system, such that an exact adjustment of the transport speed is ensured.

It was surprisingly found that, with the transport conduit having a standard diameter of 0.5 to 3 mm, or preferably 1 to 2 mm, an exactly adjusted and preferably constantly maintained transport speed of 1 to 10 m/min, or preferably 2.5 to 3.5 n/min, permits gentle transport of the sample of biological material and in particular of living cell material. Permitted variation of the transport speed is 30%, preferably at most 2%.

With the method according to the invention, biological material and in particular living cell material could be transported through the conduits from several reactors over a longer distance and with less variation in the transport speed, without interruption and thus particularly gently and without losses. This was demonstrated for hybridoma cells and SF9 insect cells. With suspensions of mechanically sensitive material and in particular of living cells, maintaining a defined transport speed is preferred, since, if the transport speed is too fast, the material is destroyed, e.g. because of shearing forces, and, if the transport speed is too slow, the material could settle as a sediment in the horizontally routed conduit. The transport is preferably effected pneumatically or with liquids.

In a particular embodiment, the burets also ensure the aliquoting of the sample.

If analysis of a cell-free sample is wanted, the cells can be separated off by filtration by adjusting the pore width of the filter directly on the probe head of the sampling valve. Alternatively, the sample can be filtered in the preparation station or can be collected in a vessel in order to form a sediment therein. After the sedimentation, a cell-poor sample can be removed from the supernatant, filtered and delivered to an analyzer. An alternative that does not use a filter and thus requires little maintenance is for the sample to be transported at a speed of <1 n/min. In conduits that are longer than 5 m, all the cells settle as a sediment during transport, such that a cell-free sample that does not require to be filtered for further processing can be collected in a sampling vessel.

The transport conduits can preferably be temperature-controlled, preferably with a Peltier element, to a temperature of between 0° C. and 100° C., preferably of between 4° C. and 37° C. Alternatively, the temperature is controlled via a heated double-shell conduit.

The sample-transporting device preferably has two burets which are each connected by a valve island to the transport conduits, which in turn are connected to one or more sampling valves, the preparation and analysis stations and sources of air and transporting and/or cleaning fluids.

The transport conduits preferably have at least one control unit, which in particular monitors and controls flow, pressure, optical density or opacity in the transport conduits in order to avoid blocking of the conduits.

Sterility is of the utmost importance for a reliable, lengthy fermentation process. An advantage of the process analysis system according to the invention is that the sampling valve can be autoclaved together with the reactor, in particular the bioreactor, and its supply conduits are closed off by sterile connections. In addition, the sampling and sample-transporting device is preferably cleaned with steam, sterilized water or sterilizing solutions. After the analysis, the sampling valve and the transport conduit are usually flushed, preferably with steam, and heated to temperatures of usually between 100 and 135° C. in order to eliminate any cell residues and to sterilize and clean the system. Alternatively, the cleaning can also be done using sterile water or sterilizing irrigation solution. Sterile, dry air is then usually conveyed through the sampling valve and the conduit in order to cool and dry the sample-transporting system. At the rear valve interior, the sampling valve preferably also has an auxiliary nozzle that serves for better in-situ cleaning of the sampling valve. The auxiliary nozzle can be used to ensure that no air bubble unfavorable to cleaning forms in the rear valve interior, and that no dead space forms in the upper part thereof.

After the sample has been transported and then analyzed and documented, the sampling and sample-transporting device, and in particular the sampling valve and transport conduit, are usually cleaned thoroughly with clean-in-place media and dried with sterile air.

It is important to ensure adequate flushing with demineralized water during the last clean-in-place or sterilization-in-place procedure, in order to prevent formation of a coating on the surfaces that come into contact with the product in the subsequent drying process.

The present invention permits fully automated analysis of samples, including sterile sampling, transport, preparation and analysis under sterile conditions with integration of the analysis values by direct connection to a process control system and/or a programmable controller for regulating and controlling the process. It ensures in particular the removal of small samples of defined volume and gentle transport in particular of cell-containing samples, and, if appropriate, cell separation and liquid sample preparation and analysis. The present invention permits flexible configuration of the working procedures and an automatic adaptation of the sample preparation and aliquoting to the requirements of the working procedures and also of the analyzers available in the system.

A great advantage of the process analysis system described here for bioprocesses is also that several bioreactors can be operated independently of one another. Each valve can be controlled decentrally and, therefore, independently. Furthermore, it is conceivable for several reactors which work with different cell lines and produce different products to be operated by a single process analysis system and therefore particularly inexpensively, since an ingenious cleaning management system avoids mutual contamination of the individual bioreactors.

This is a much more cost-effective, more flexible and more reliable alternative to the systems hitherto available on the market, since different samples from several bioreactors are collected, processed and evaluated in a central "intelligence", and it is not necessary to provide an expensive analysis system for each individual bioreactor. Moreover, integrated automation units allow bioprocesses to be regulated and controlled.

BRIEF DESCRIPTION OF THE DRAWINGS

The following figures illustrate the invention without limiting it.

FIG. 3*a*: illustrates a downwardly inclined installation of the sampling valve FIG. 3*b*: illustrates a horizontal installation of the sampling valve, with the sample chamber inclined relative to the nozzle axis FIG. 3*c*: illustrates a 90° downwardly inclined installation of the sampling valve

LIST OF REFERENCE NUMBERS 1 bioreactor
2 sampling valve
3 sample chamber
4 transport conduit
5 moderate gas pressure
6 continuous plug
7 target location
8 buret
9 retained samples
10 sample analysis
11 data output and stored in database
12 computer system
13 automation system
14 standardized fermenter nozzle
15 spring
16 front sealing element
17 rear sealing element
18 connection shaft
19 membrane
20 retainer plate
21 pressure plate
22 lifting cylinder
23 sealing device
24 admission opening
25 outflow nozzle
26 auxiliary nozzle
27 screw connection
28 sealing device
29 sealing device
30 sealing device
31 inlet channel
32 probe head
33 control
34 guide mounted on connection shaft
35 valve
36 rear valve interior
37 quick-closure coupling
38 coupling pieces
39 filter
40 sealing device
41 cap
42 valve stem
43 pores
44 three-way cock
45 sampling valve
46 decentralized control and supply unit
47 decentralized local control of manual sampling
48 central automation unit
49 check unit
50 manual sampling
51 buret 1
52 buret 2
53 central collecting vessel
54 probe
55 agitator
56 cell counter
57 analyzer 1
58 analyzer 2
59 chromatography system
60 biosensor
61 waste vessel
62 filter
63 compressed air
64 water
65 cleaning medium
66 transport medium
67 steam generator
68 valve
69 valve
70 aliquoting FIG. 1*a* shows the opened sampling valve (2) installed in a bioreactor (1), with a sample chamber (3) of defined volume into which the sample initially flows when the valve is opened. The rear sealing element (17) delimits the sampling volume and permits removal of a small, defined volume. The front sealing element (16) avoids further liquid being able to flow out of the bioreactor into the sampling valve. After closure of the valve (FIG. 1*b*), the path to an attached transport conduit (4) is freed. The sample is then transported as a substantially continuous plug (6) to the target location (7), a central sample preparation and/or analysis station. The preferred use of two burets (8) permits, by suitable interaction, a continuous speed of transport and, therefore, particularly gentle transport, without loss, through the conduit. The cell suspension is collected in a sample-collecting vessel. The various measures for sample analysis (10) are then carried out there, e.g. aliquoting, cell separation, use of various analysis methods, or the closure, identification and freezing of the retained samples (9). Finally, after the measurement results have been scanned, data are output and stored in a database in a computer system (12) in a manner appropriate for quality assurance. The analysis results are then transferred to an automation system (13).

Figure 1A:
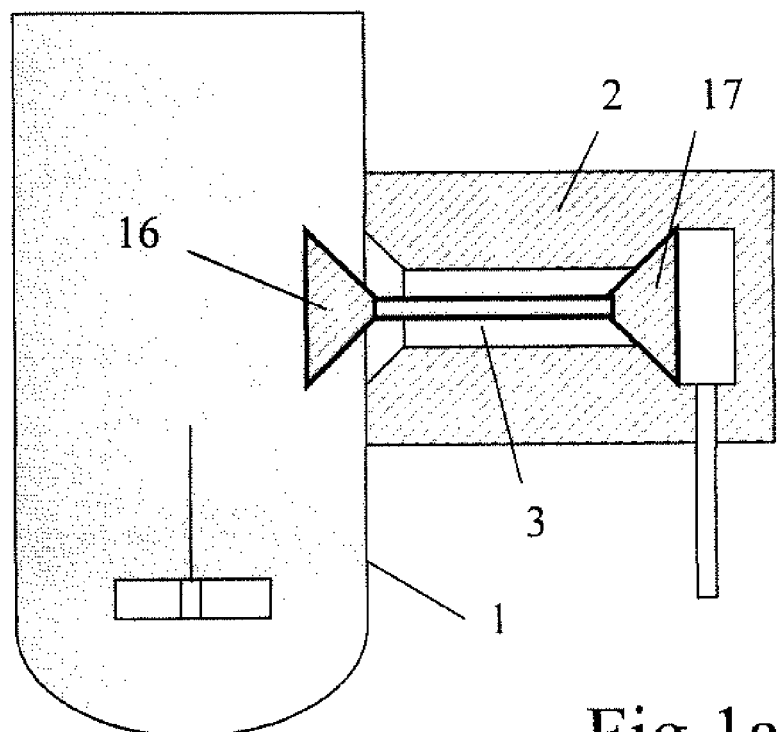
FIG. 1a: illustrates a sampling valve in the opened state on a bioreactor
Figure 1B:
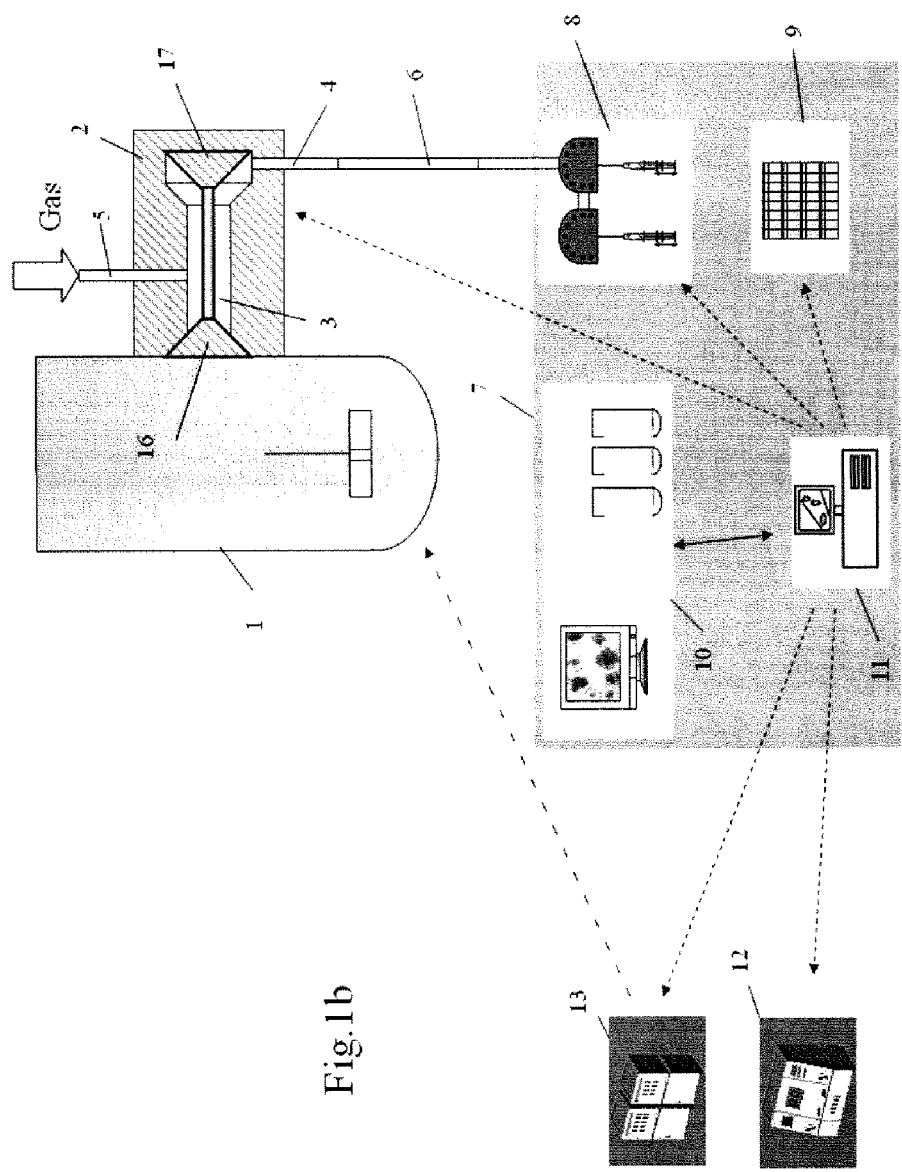
FIG. 1b: illustrates a sampling valve in the closed state on a bioreactor
Figure 2:
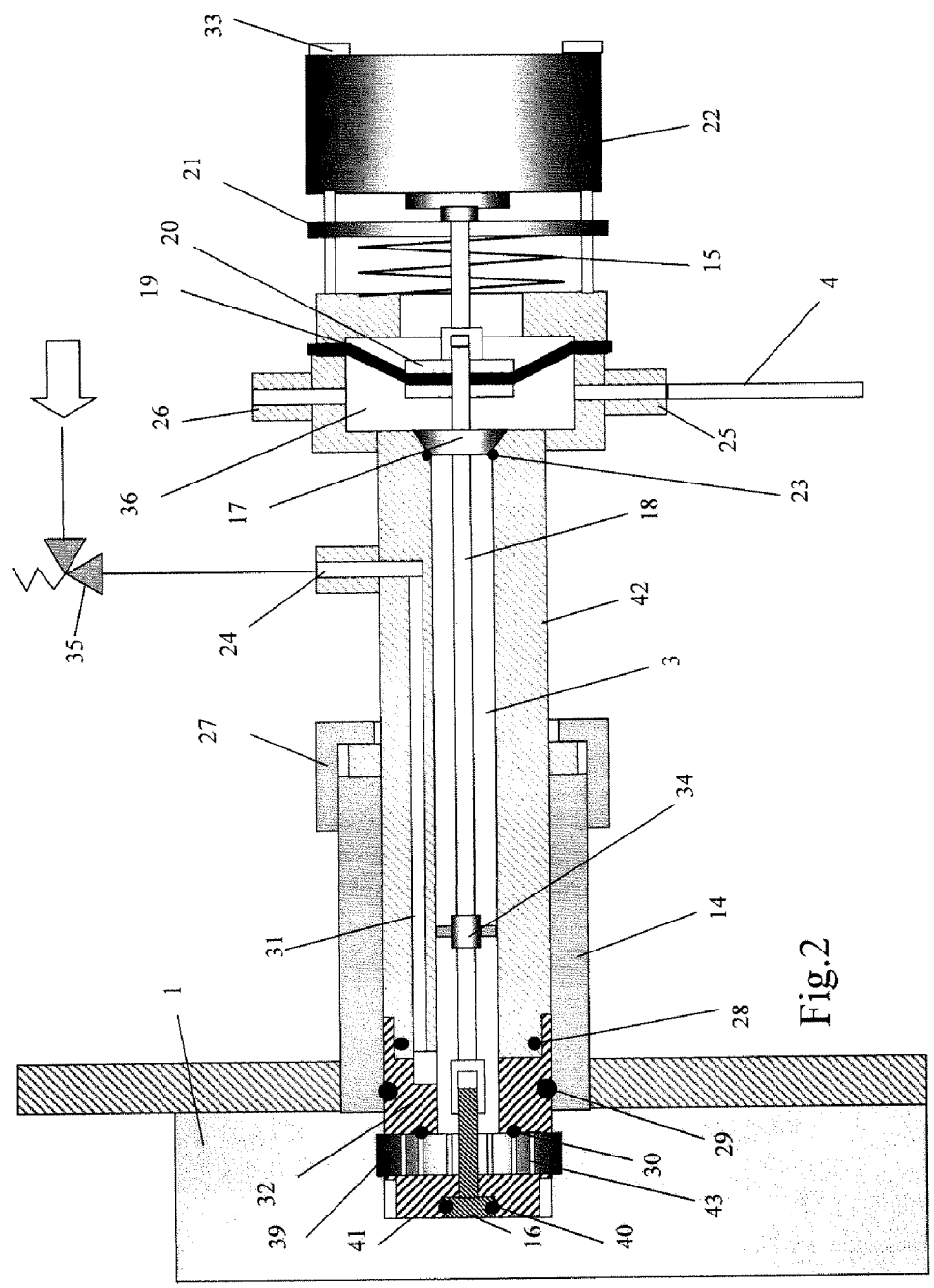
FIG. 2: is a side view of the sampling valve in the opened state

As is shown in the illustrative embodiment in FIG. 2, the sampling valve (2), analogously to standard probes, is fitted with the aid of a screw connection (27) into standardized fermenter nozzles (14) with the diameter of DN25. The sampling valve (2) is sealed inside the nozzle by a sealing device (29), preferably what is called an O-ring. In the energy-free state, the sampling valve (2) is closed to the reactor space by a rear sealing element (16). The closure force is transmitted by pretensioning of the spring (15), preferably a spiral spring, from the pressure plate (21) to the rear sealing element (17) via the connection rod (18). The rear sealing element (17) provides sealing by being pressed against the valve stem (42) by means of a sealing device (30), preferably an O-ring. When the valve is opened by actuation of the autoclavable lifting cylinder (22), a pressure force directed counter to the restoring force of the spring (15) is transmitted to the guide rod (18). A membrane (19), which is squeezed between two retainer plates (20), is mounted on this guide rod (18). The pressure force on the guide rod leads to deflection of the membrane (19), which hermetically seals off the sample chamber (3) and the rear valve interior (36) from the environment. At the same time, the front sealing element (16) is opened in the direction of the interior of the bioreactor, and the rear sealing element

(17) is closed against the cylindrical sample chamber (3) and sealed off by a sealing device (40). In this opened state of the valve, the air bubble enclosed in the sample chamber (3) escapes into the bioreactor (1), and a sample of defined volume flows from the bioreactor into the sample chamber (3). At the probe head (32), the sampling valve is protected by a self-cleaning filter (39), such that no large aggregates can enter the sample chamber (3) and the transport conduit (4). This filter (39) surrounds part of the probe head and prevents aggregates from passing into the valve. The width of the pores (43) of the filter is 0.5 mm to 2 mm, preferably 1 mm. For removal of cell-free samples, a filter surface with a pore width of 0.02-2 µm, preferably 0.45 µm, can be used. In the open state, a cap (41) is driven out in the direction of the fermenter, thus forming an opened area. Some pores (43) are depicted as white boxes, through which a sample can pass into the valve from all directions. After the lifting cylinder (22) is released via a control (33), which is done pneumatically, the valve closes. The cap (41) is moved in the direction of the valve and fills the hollow chamber of the filter (39) from inside, i.e. the pores (43) are closed off from the inside by the cap (41). The guide (34) mounted on the connection shaft serves for secure positioning of the sealing surfaces. To transport the sample, gas or liquid is introduced through the admission opening (24) and an inlet channel (31) and slowly displaces the sample from the sample chamber (3) into the rear valve interior (36) and to the outflow nozzle (25). The admission opening is protected via a valve (35), preferably a check valve. The auxiliary nozzle (26) additionally arranged on the rear valve interior (36) allows better in-situ cleaning. In order to reduce the load on the membrane, the rear valve interior (36) has a greater diameter than the sample chamber (3). The auxiliary nozzle (26) prevents formation of an air bubble unfavorable to cleaning and thus prevents a dead space in the upper part of the rear valve interior (36). For sample transport, the sample is conveyed under gas pressure or by a liquid through an outflow nozzle (25) into the transport conduit (4).

FIG. 3a shows a preferred embodiment with downwardly inclined installation of the sampling valve (2) on the bioreactor wall.

FIG. 3b shows another preferred embodiment of the valve, the cylindrical sample chamber (3) itself being inclined relative to the nozzle axis.

FIG. 3c shows another preferred embodiment of the valve with a 90° downwardly inclined installation of the sampling valve (2) on the bioreactor wall.

Figure 4:
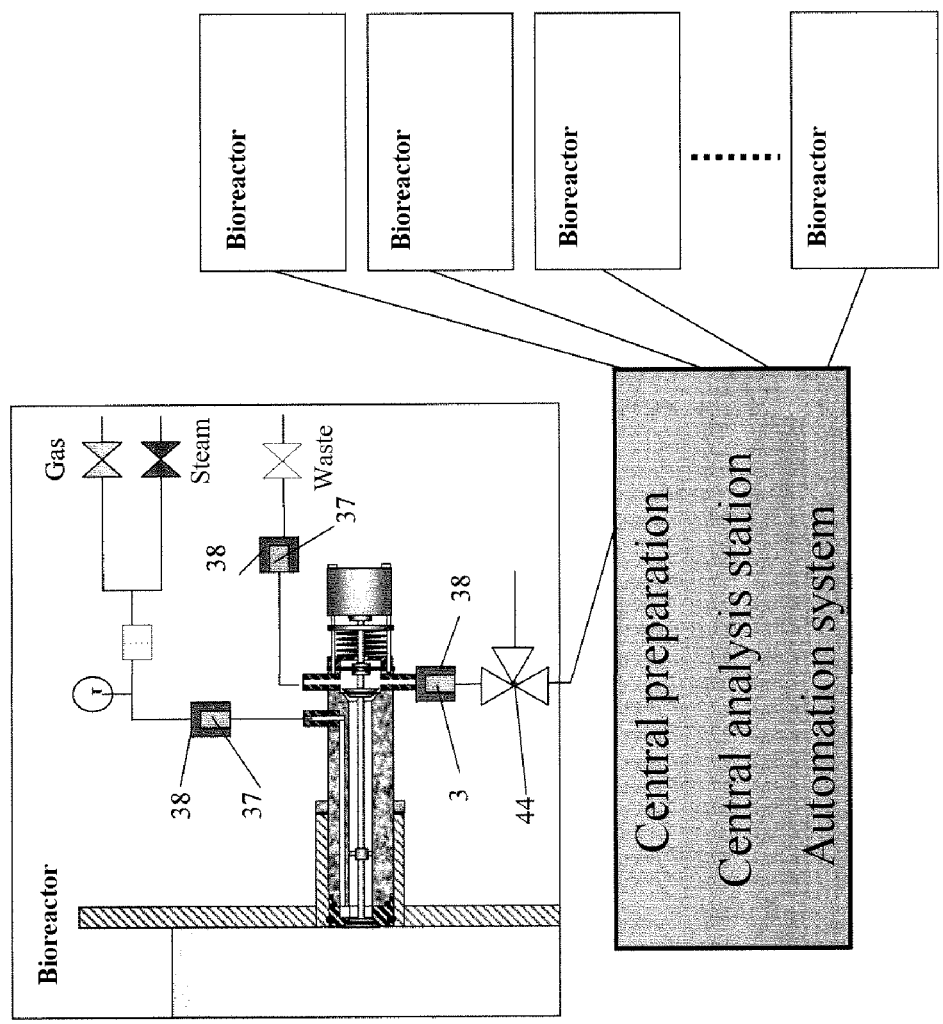
FIG. 4: illustrates connection of several bioreactors to a central analysis station

FIG. 4 shows a possible way of coupling the sampling valve to the conduit system, composed of supply conduit, cleaning conduit and transport conduit, by autoclavable and steam-sterilizable quick-closure couplings (37) which, in the disengaged state, have a closure mechanism that protects the sterile inner surfaces of the two coupling pieces (38) against contamination. The sample is transported into a central sample preparation and/or sample analysis station (7). In addition, several bioreactors can be used which operate independently of one another. Each valve can be actuated decentrally and thus independently.

Figure 5:
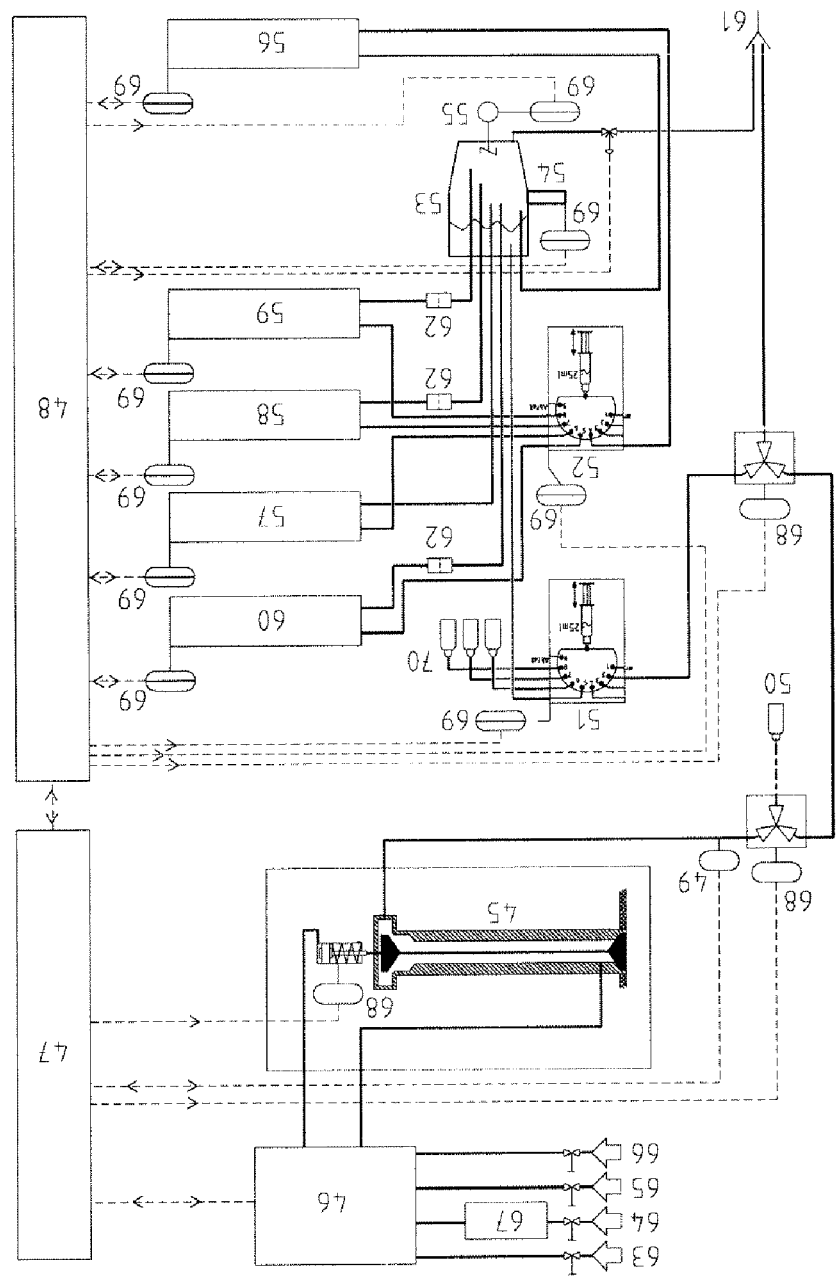
FIG. 5: illustrates sample transport, preparation and analysis, and control and regulation of a bioprocess

FIG. 5 shows a central sample preparation and/or sample analysis station, for the sake of clarity only with one sampling system (45). Supply conduits are shown as continuous lines, while component controls are represented by broken lines. The arrows on these lines in each case indicate the direction of communication. The process analysis system has a decentralized control and supply unit (46) with decentralized on-site operation (47) at each sampling system. This communicates via a central automation unit (48). The decentralized control and supply unit (46) regulates the delivery of compressed air, steam, cleaning liquids and transport liquids. A control unit (49) is integrated in the transport conduit between the sampling system (2) and a three-way cock (44). The three-way cock (44) permits manual sampling (50). Two burets (51, 52) are actuated by the automation system in order to ensure the transport and aliquoting (70) of the sample. The sample is transported into a central collecting vessel (53). There, a probe (54) characterizes the sample, and an agitator (55) is additionally integrated. A signal is transmitted to the automation system in order to decide whether the sample can be diluted for further processing, concentrated or remain untreated. From the collecting vessel, the sample is distributed to various analyzers: an unfiltered sample is examined in a cell counter (56) or in analyzer 1 (57). Another part of the sample passes through a filter (62) and is distributed among analyzer 2 (58), chromatography (59) and/or a biosensor (60). All the analyzers (56-60) are connected to a waste vessel (61), although, for the sake of clarity, the connection is not shown. The analyzers can be combined in any desired number and arrangement. If different preparatory steps are needed for different analyzers, the sample in the central collecting vessel (53) can be suitably prepared for each individual analyzer. All measurement values are transferred to the automation system in order to regulate and/or control the bioprocess. All the samples are collected in a waste vessel (61).

Figure 6:
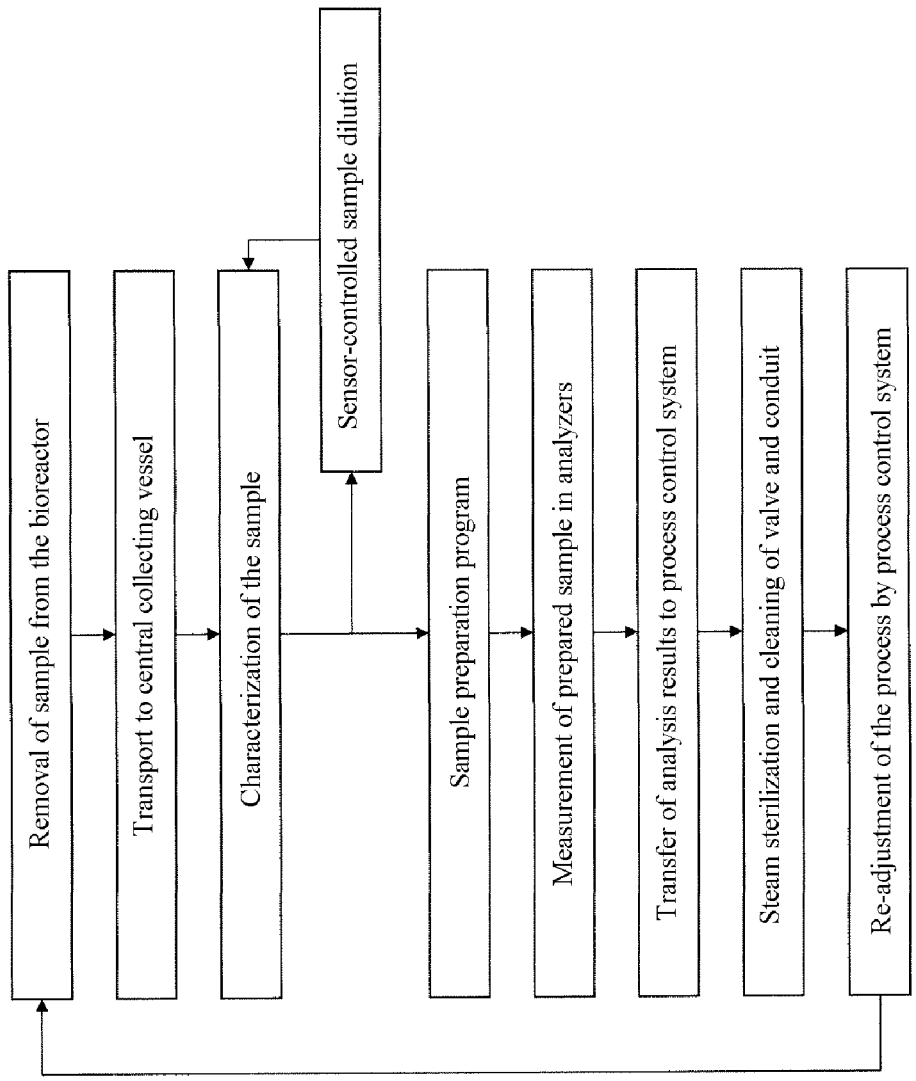
FIG. 6: is a flowchart illustrating the process of the invention.

FIG. 6 shows a flow chart. After the sample has been removed from the bioreactor, the whole sample is transported gently into a central collecting vessel. In a preliminary examination, a sensor characterizes the sample. If the concentration is too high, a sensor-controlled sample dilution program is started. This is repeated until the sample is within the desired concentration range. Thereafter, the sample preparation program is started and the sample is measured in the various analyzers. The analysis results are transferred to a process control system. After completion of all the measurements, the steam sterilization and cleaning of the valve and conduits are started. The process control system uses the analysis results to adjust the process.

EXAMPLES

The following examples confirm the usability of the sample analysis system according to the invention without limiting the system to this use.

Example 1

With the aid of the sampling valve according to the invention, a 12 ml sample of SF9 insect cells was removed from a bioreactor and transported through a hose (internal diameter 1.5 mm, length 10 m) at a speed of 3 m/min in the sample analysis system according to FIG. 5. One sample was removed by hand from the bioreactor and measured, and one sample was removed with the sampling valve, transported by the sample-transporting device and measured. With the aid of the CEDEX analyzer (Innovatis), it was determined there that the proportion of living cells to dead cells was identical before and after transport. Moreover, at the cell determination station (56), it was established, using the CEDEX analyzer, that the rate of recovery of the cells was >90%. This confirmed the usability of the sample analysis system according to the invention for removal and transport of living cells.

Example 2

With the aid of the sampling valve according to the invention, a 10 ml sample of hybridoma cells, which produce antibodies to fight tumors, was removed from a bioreactor and transported through a hose (internal diameter 1.5 mm, length 5 m) at a speed of 3 m/min in the sample analysis system according to FIG. 5. One sample was removed by hand from the bioreactor and measured, another sample was removed with the sampling valve, transported by the sample-transporting device into the process analysis system and measured. With the aid of the CEDEX analyzer (Innovatis AG), it was determined there that the proportion of living cells to dead cells was identical before and after transport. Moreover, at the cell determination station (56), it was established, using the CEDEX analyzer, that the rate of recovery of the cells was >95%. This confirmed the usability of the sample analysis system according to the invention for removal and transport of living cells.

The invention claimed is:

1. A sampling valve for removing a sample of defined volume from a bioreactor with reduced mechanical loading of the sample, comprising a sample chamber of defined volume having an inlet adapted for installation through a wall of said bioreactor or in a nozzle on a wall of said bioreactor, and an outlet connected to a rear valve interior, and said rear valve interior comprises an outflow nozzle connected to a transport conduit, wherein a front sealing element opens and closes the inlet and a rear sealing element opens and closes the outlet, said front and rear sealing elements being connected to opposite ends of a connecting shaft which shaft is movable by a controller between a first position and a second position in which first position the front sealing element is in an open position and the rear sealing element is in a closed position and in which second position the front sealing element is in a closed position and the rear sealing element is in an open position, whereby the inlet is open at the same time as the outlet is closed, and the outlet is opened at the same time the inlet is closed, wherein the sample chamber is further connected to an inlet channel, wherein to transport the sample, gas or liquid is introduced through the inlet channel and slowly displaces the sample from the sample chamber into the rear valve interior and to the outflow nozzle.

2. The sampling valve as claimed in claim 1, in which the connecting shaft is movable from the first position to the second position and from the second position to the first position by the actuation of a lifting cylinder by the controller.

3. The sampling valve as claimed in claim 2, in which the lifting cylinder is driven pneumatically or electrically.

4. The sampling valve as claimed in claim 1, in which a closing force is transmitted by a spring from a pressure plate to the rear sealing element via a connection shaft.

5. The sampling valve as claimed in claim 1, in which a guide rod is mounted on the connection shaft for secure positioning of the sealing elements.

6. The sampling valve as claimed in claim 5, in which a membrane is fitted on the guide rod.

7. The sampling valve as claimed in claim 1, further comprising a self-cleaning filter at the inlet.

8. The sampling valve as claimed in claim 1, in which the defined volume is 2 to 200 ml.

9. The process analysis system of claim 8, comprising a self-monitoring facility.

10. The process analysis system as claimed in claim 9, wherein the self-monitoring facility is adapted to compare the properties of the sample to the requirements of the analysis station and control preparation of the sample.

11. A process analysis system, comprising a device for removal of a sample from a reactor, a sample-transporting device, optionally an aliquoting and/or sample preparation station, and at least one sample analyzer, wherein the device for removal of a sample is the sampling valve of claim 1.

12. The process analysis system as claimed in claim 11, connected to an automation system for guiding, controlling and/or regulating the process in a reactor.

13. The process analysis system as claimed in claim 11, wherein the sample-transporting device comprises transport conduits and at least one system for accelerating the sample or aliquot through the transport conduit from at least two burets, the burets being operated with the following steps:
  a) a first buret is filled,
  b) shortly before the first buret has reached its fill limit, a second buret is filled and takes over the transport, the sample experiencing neither additional acceleration nor a brief intermediate stop,
  c) the first buret is uncoupled from the transport conduits and emptied again, such that it is once again available,
  d) steps a) to c) are repeated, and, with the transport conduit having a diameter of 0.5 to 3 mm, the sample or aliquot is conveyed at a predefined transport speed of 1 to 10 m/min.

14. A method for controlling one or more independently operating reactors which comprises monitoring each reactor with the process analysis system of claim 8, and adjusting reactor conditions in accordance with the results of that analysis.

15. The process analysis system of claim 8 wherein the sample analyzer carries out biochemical analysis of reaction products and secondary components.

* * * * *